United States Patent [19]

Draenert

[11] Patent Number: 4,895,146
[45] Date of Patent: Jan. 23, 1990

[54] SURGICAL BONE-GRINDING INSTRUMENT

[76] Inventor: Klaus Draenert, Alte Landstrasse 26, D-8012 Ottobrunn, Fed. Rep. of Germany

[21] Appl. No.: 290,863

[22] Filed: Dec. 29, 1988

Related U.S. Application Data

[63] Continuation of Ser. No. 548,884, filed as PCT EP83/00007 on Jan. 17, 1983, published as WO83/02553 on Aug. 4, 1983, abandoned.

[30] Foreign Application Priority Data

Jan. 25, 1982 [DE] Fed. Rep. of Germany ....... 3202193

[51] Int. Cl.$^4$ ............................................. A61B 17/32
[52] U.S. Cl. ...................................... 606/79; 128/754; 606/180
[58] Field of Search .............. 128/303 R, 305, 310, 128/92 R, 92 E, 754, 755

[56] References Cited

U.S. PATENT DOCUMENTS

| | | | |
|---|---|---|---|
| 847,133 | 3/1907 | Velasco | 128/310 |
| 930,477 | 8/1909 | Hudson | 128/310 |
| 2,147,175 | 2/1939 | Rolland | 128/92 R |
| 2,261,230 | 11/1941 | Cox et al. | 128/310 |
| 2,326,908 | 12/1942 | Williams | 255/72 |
| 2,504,075 | 4/1950 | Karle | 128/310 |
| 2,710,000 | 6/1955 | Cromer et al. | 128/754 |
| 2,919,692 | 1/1960 | Ackermann | 128/754 |
| 3,512,519 | 5/1970 | Hall | 128/754 |
| 4,122,855 | 10/1978 | Tezel | 128/310 |
| 4,274,769 | 6/1981 | Multakh | 408/145 |
| 4,509,115 | 11/1977 | Jumashev et al. | 128/310 |
| 4,512,344 | 4/1985 | Barber | 128/755 |
| 4,649,918 | 3/1987 | Pegg et al. | 128/754 |

*Primary Examiner*—John D. Yasko
*Attorney, Agent, or Firm*—Kinney & Lange

[57] ABSTRACT

The invention relates to a bone-grinding instrument, in which the grinding head is joined, releasably via a coupling, to a driving part, wherein the grinding head is designed as a hollow cylinder with a rounded end face and is provided on the outer and/or inner wall with an abrasive coating having a particle size between 30 and 300 μm, and to a hollow removal cylinder which is to be used together with this bone-grinding instrument. In place of an abrasive coating, this hollow removal cylinder has barbs, which penetrate into the bone core.

10 Claims, 3 Drawing Sheets

SURGICAL BONE-GRINDING INSTRUMENT

This is a continuation of application Ser. No. 548,884, filed as PCT EP83/00007 on Jan. 17, 1983, published as WO83/02553 on Aug. 4, 1983, now abandoned.

The invention relates to a device for removing bone material and for preparing bones for the insertion of implants, which device works with a water flush, in accordance with the principle of grinding.

For taking bone biopsies and bone transplants, and for preparing an implantation bed, bone cutters have hitherto been used which are designed as cutting, chip-forming drills or hollow drills with an end face having sharp teeth, such as the so-called Burkhardt cutter. These cutters have considerable disadvantages, since they lead to significant tearing of soft parts or cutting injuries or lacerations, if they slide off into the soft tissues during working. Although the bone cutters designed as hollow drills preserve the bone cylinder, they cause destruction in the removal bed. The cutters designed as drills preserve the removal bed, but destroy the cylinder being removed.

The bone structure of samples removed by means of such hollow drills shows multiple injuries, since the bone is cut and partially broken and splintered. The edge parts of the marrow tissue are injured and torn out in the same way as blood vessels, so that the morphological structure of the biopsy cylinders frequently is extensively destroyed in the edge zones. Corresponding destruction also occurs in the edge zones of a removal bed prepared by means of a drill and makes the settling of implants more difficult.

The invention is based on the object of providing a device which permits the removal of bone cylinders (biopsies) with an intact edge structure and the preparation of implant beds with an intact edge structure and which cannot cause any lacerations of soft parts, when it slides off.

The surgical cutting tool known from U.S. Pat. No. 3,384,085 works like dental drilling instruments with a very high speed of rotation of more than 100,000 rpm. As in other known cutters and drills, however, the tool heads are formed with sharp edges and have therefore not only a cutting action, but also a tearing action. Moreover, with tools which penetrate more deeply into the bone, it is also no longer possible to remove the heat of friction, caused by the very fast rotation, to a sufficient extent so that tissue is damaged by overheating.

German patent specification No. 808,360 has disclosed a device, not described in more detail, for the removal of bone substance, which device consists of a rotary body covered with small, angular smooth teeth and preferably with removal channels. However, this rotary body allows only cutting of the bone substance with the formation of chips, so that bone pulp is formed. The temperature thus arising leads to osteonecroses and to necrotic denatured tissue paste.

It has now been found that the stated object can be achieved when the instrument is designed as a grinding tool. In addition, it is important that heat removal during the grinding process is ensured by supplying a coolant.

To achieve the stated object, the bone-grinding instruments, having the features indicated in the claims, are used according to the invention.

The invention is explained by the description below of an illustrative embodiment which refers to the attached drawings in which.

Figure 3:
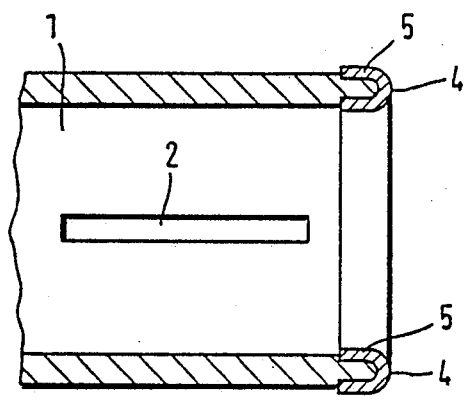
Figure 4:
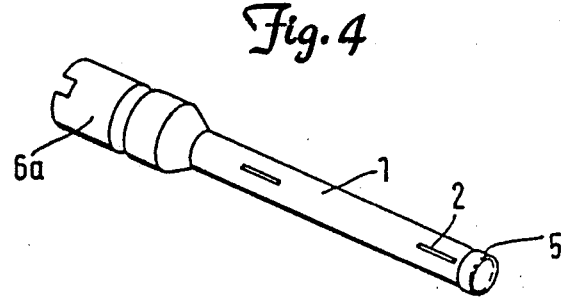
Figure 5:
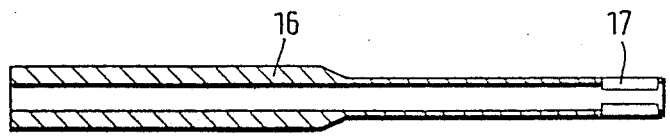
Figure 6:
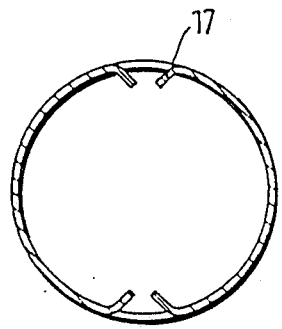
Figure 7:
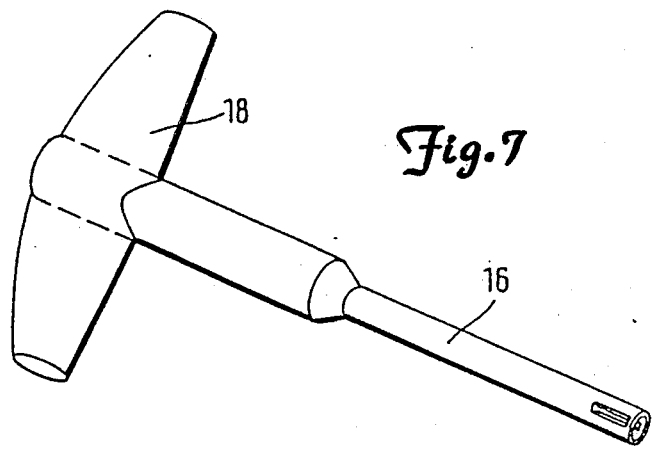
Figure 8:
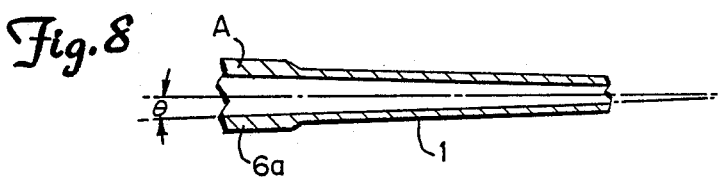

FIG. 3 shows an enlargement of the end face of the hollow cylinder, in longitudinal section, FIG. 4 shows a view of the exchangeable hollow cylinder, FIG. 5 shows a diagrammatic longitudinal section of a hollow removal cylinder suitable for use with the device according to the invention, FIG. 6 shows a cross-section through the hollow removal cylinder, FIG. 7 shows a view of a hollow removal cylinder fitted with a handle, and FIG. 8 is a partial view of a hollow cylinder showing that at least the internal wall of the cylinder is conical with the conical angle exaggerated for emphasis.

Figure 1:
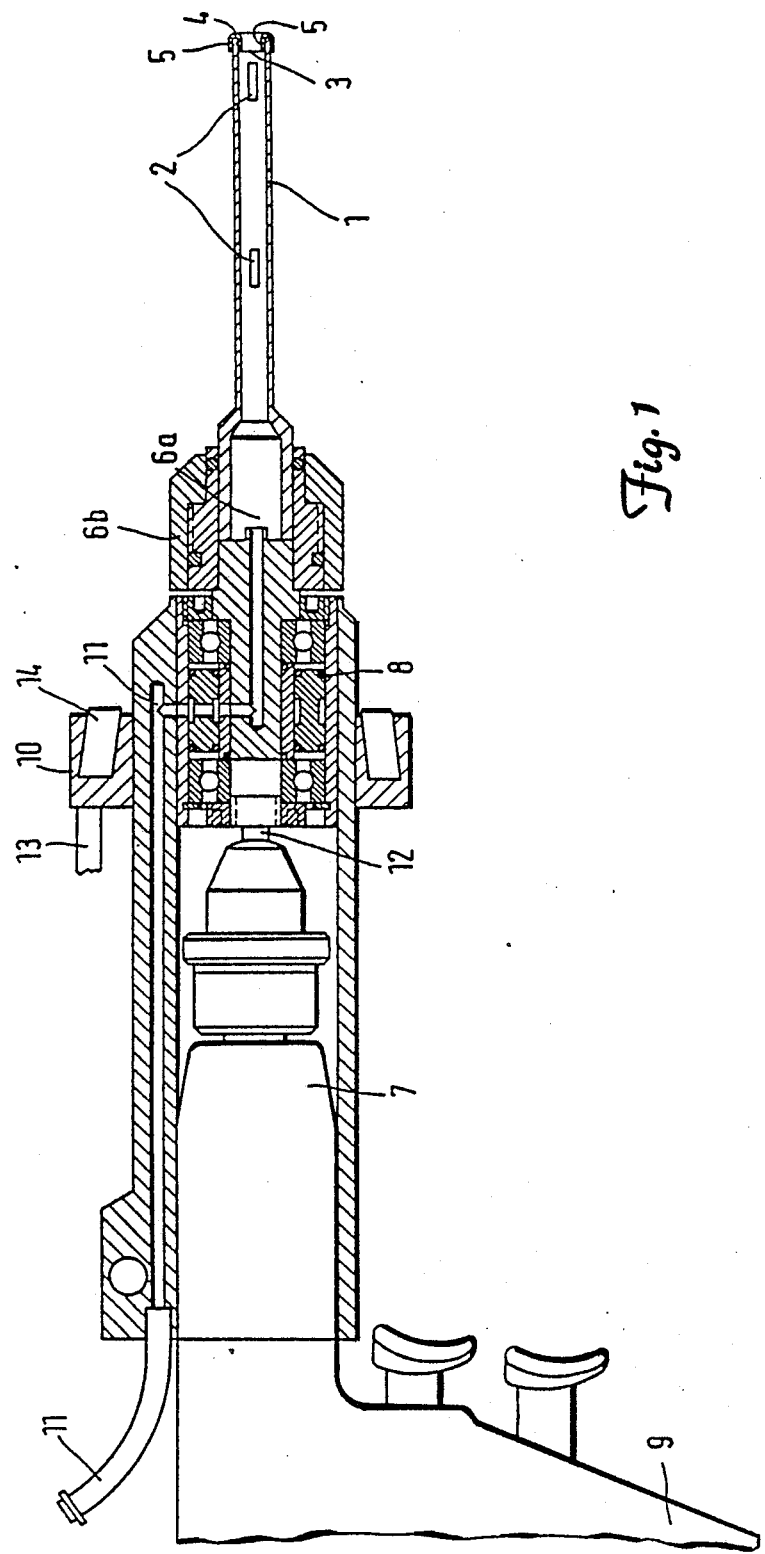
FIG. 1 shows a diagrammatic longitudinal section of the device.
Figure 2:
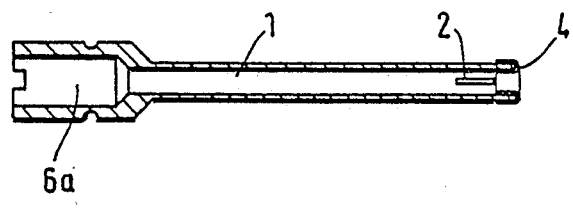
FIG. 2 shows a diagrammatic longitudinal section through the hollow cylinder.

The numbers in the drawings have the following meanings:

1—Hollow cylinder
2—Longitudinal slots
3—Grinding head (front part of 1)
4—End face of 1
5—Abrasive coating (inside and outside)
6a—Coupling part
6b—Coupling part of the driving part 7
7—Driving part
8—Rotary seal
9—Handle
10—Illumination device
11—Coolant feed line
12—Drive pinion
13—Optical fibre bundle
14—Light outlet aperture
16—Hollow removal cylinder
17—Barb
18—Handle The surgical instrument, illustrated in FIG. 1, shows an elongate hollow cylinder (1) as the grinding tool. On one end, this cylinder has a coupling part (6a) which can be joined to the coupling part (6b) of the driving part (7), by means of which the hollow cylinder (1) can be driven in rotation at an adjustable speed by means of the driving mechanism (7) shown diagrammatically. The end face is labelled (4). The internal cross-section of the hollow cylinder (1) increases uniformly and slightly from the end face (4) up to the outlet of the coupling part (6a), in order to make it easier to force out the drilled bone cylinder. In the front region, near to the end face (4), the hollow cylinder (1) has longitudinal slots (2) which preferably run axially.

The longitudinal slots (2) allow the coolant supplied to flow out.

In the front region, forming the grinding head (3), of the hollow cylinder (1), that is to say preferably between the longitudinal slots (2) and the end face (4), the hollow cylinder (1) carries a durable abrasive coating (5) on its inner wall and/or outer wall; the end face (4) is rounded so that the greatest possible surface area of coating comes into contact with the bone.

The hollow cylinder (1) is preferably made of stainless steel, which as a rule is used in a highly polished form, such as is customary for precision instruments. The wall thickness of the hollow cylinder (1) varies as a function of its diameter, but is normally between 0.09 and 0.90 mm, preferably between 0.1 and 0.5 mm. As is seen in FIG. 8 at least on the inside, the hollow cylinders have a slightly conical shape. Advantageously, they have an inside clearance angle 0 from 5 seconds up to 180 seconds, preferably 20 second to 72 seconds.

The abrasive coating (5) has a layer thickness of about 100 to 700 μm, preferably up to 500 μm. It can consist of a conventional resistant material, for example diamond, corundum, alumina ceramics, glass, boron nitride or comparably hard materials. The particle size is matched to the diameter of the grinding head and to the nature of the bone to be drilled and ranges from 30 to 350 μm, and specifically from 50 to 150 μm for compact bone substance and about 150 μm for spongy bone substance. A particularly suitable particle size is about 50 μm for grinding head diameters of about 2 to 8 mm, about 80 μm for diameters of about 8 to 12 mm and 100 μm for diameters greater than 20 mm.

In the case of a diamond coating, the particle size is preferably between 30 and 250 μm, and at 350 μm as a maximum.

The coating (5) is applied in a conventional manner, for example by electro-deposition or by direct or indirect sputtering. In the case of large cylinders, fitting in a soft alloy can also be envisioned.

The end face (4) of the hollow cylinder (1) should be rounded, so that an optimum of abrasive grain comes into contact with the bone substance which is to be ground.

The number of slots (2) in the hollow cylinders (1) depends on the size of the hollow cylinders, that is to say on the internal diameter. Holes have a diameter between 200 and 1000 μm, and retangular windows have a length of 2 to 6 times the indicated width of 0.3 to 0.8 mm.

The diameter and length of the hollow cylinders (1) are matched to the nature of the surgical intervention to be carried out. The smallest cylinders of such a set are provided with a diamond coating of particle sizes of about 50 μm and are intended for fine bone biopsies, predominantly for compact bone substance or for sternal punctures, skull cap biopsies, and biopsies for assessing the progress of the healing of bone fractures.

By means of its coupling part (6a), the hollow cylinder (1) can be inserted into a corresponding coupling part (6b) of the driving part (7). The driving part (7) has a rotary seal (8), in which the coolant feed line (11) ends, and a drive pinion (12) on which the chuck of the drive head of the drive mechanism (7), which can be inserted into the driving part, engages. The driving mechanism can be a conventional drill. The coupling part (6b) is rotatably and undisplaceably mounted in the driving part, for example by means of a plastic bearing or ball bearing. The driving part (7) can preferably be made of a light metal alloy and is likewise a precision component.

A physiological solution, such as physiological saline or Ringer solution or a suitably adapted solution, passes through the coolant feedline (11) into the hollow cylinder (1), where it leaves through the longitudinal slots (2). A special feature of this central water path is the pressure build-up due to the rotation of the hollow grinding cylinder. This is controlled by the fenestration of the cylinder. The water is fed in via a rotary seal. The water flush is arranged centrally, which has the advantage that a pressure builds up in the hollow cylinder (1) and, primarily, a high starting pressure is not required. A sterile infusion bottle above the operating table at a height of between 50 cm and 120 cm is sufficient. The coolant line is provided with a nonreturn valve (not shown), which interrupts the coolant feed when the drill is at a standstill.

In addition, an illumination device (10) which may be removable and which emits light beams focussed on the grinding head (3) is provided on the driving part (7). For feeding the light in, the illumination device can, for example, have an optical fibre bundle (13) which passes the light to the light outlet apertures (14). If quartz fibres are used as the optical fibres, ultraviolet light can also be transmitted, in order to make, for example, tetracyclin-marked bone biopsies (in the case of tumors) or fluorescent plastic residues (in the case of replacing a prosthesis) more readily visible.

In addition to this annular, screwed or permanently fitted multi-point glass fibre illumination, a central glass-fibre light-rod focussed on the grinding head (3) is additionally provided in the case of large instruments, such as are used for preparing the bone cavity for a change of prosthesis.

For the transplantation of cartilage and bone transplants, an instrumentality comprising so-called twin hollow cylinders are envisaged, that is to say a set of two hollow cylinders of equal length, the diameters of which differ by 0.1 to 0.4 mm, so that the removal cylinder can be inserted into a donee bed which is 0.1 to 0.4 mm smaller. Since above all spongy bones are slightly elastic and can readily be compressed on insertion, stable implantation without extraneous materials is ensured in this way. The magnitude of the difference in diameters depends directly on the diameter of the hollow cylinder. Hollow cylinders of 4.5–8.5 mm internal diameter differ by 0.2 mm, smaller hollow cylinders by 0.1 mm, and larger ones of 10 to 35 mm diameter differ by 0.2 or a maximum of 0.4 mm. Twin hollow cylinder grinders for compact bones differ by 0.05 to 0.1 mm. In each case, the cylinders are measured after coating and mutually allocated.

The bone-grinding instrumentality comprises a first cylinder for removing the bone plug or bone core and a second cylinder for making an implantation bed. The cylinder for making the implantation bed is slightly smaller than the cylinder for removing the core so that the core can be forced into the bed and fit tightly within the bed as the core expands.

To remove the bone core or plug produced on drilling by the hollow cylinder 1, a hollow removal cylinder is preferably used, which is shown in FIG. 5 by way of example. This hollow removal cylinder (16) resembles the particular hollow grinding cylinder with respect to wall thickness, but it is not provided on the outside with an abrasive coating, but is provided on the inner wall with fine barbs (17) (for example 1–10). Preferably, these barbs are three-edged within the cross-sectional profile of the hollow removal cylinders (FIG. 6). They can, for example, be soldered on or punched in. After the hollow grinding cylinder has been withdrawn, the hollow removal cylinder is carefully knocked in over the bone core which has remained standing and then slightly rotated, whereby the root of the bone core is twisted off and can be withdrawn, since the barbs of the removal cylinder hook themselves into the bone frame or bone substance. The bone cylinder can then without difficulty be knocked rearwards out of the hollow removal cylinder. Preferably, the hollow removal cylinder (16) is provided with a handle (18) (compare FIG. 7).

With advantage, the instruments according to the invention form an instrumentality which can also be used for the preparation of the implantation bed. The advantage is that the device according to the invention leaves a solid bone cylinder standing, so that the implant only displaces bone substance corresponding to the wall thickness of the hollow grinding cylinder. If the implants are perforated, only slight bony regeneration is required in order to obtain a solid bony penetration of the implant. For this purpose, the instruments have in some cases flexible drill shafts, in order to enable the requisite holes to be produced which are necessary, for example, for anchoring an artificial acetabulum in the roof of the acetabulum, for taking a biopsy on the inside and outside of the iliac crest and for preparing the implantation bed for a dental prosthesis. In this way, an angle piece becomes unnecessary and central flushing with water is nevertheless possible.

The instruments according to the invention are guided by special drill guides which are provided with pointed teeth, so that the drill and grinding instrument are immovably held on the spot where bone is being removed. For the flexible shafts, special holders are necessary, by means of which the curved shaft can be firmly held on the grinding point.

Instruments for specific removal points, for example the iliac crest or sternum (breastbone), can be provided with an adjustable or fixed stop, so that cylinders of defined length can be removed.

Any commercially available drills with speeds of rotation between 500 and 5000 rpm are suitable for driving the grinders according to the invention. Drills rotating at a higher speed should be brought down to lower speeds of rotation by means of a reduction gear, since there is otherwise a risk of the cooling by the coolant being no longer sufficient.

The drill guides are preferably provided on the inside with a layer of plastic, to prevent damage to the abrasive coating of the hollow grinders by the drill guide. Since tilting can readily occur, this would be possible in the case of an all-metal design. Even though the hollow cylinder grinders, if they are carefully put in place, do not sheer off or run out in any way, as is known for sharp-toothed cutter heads, a drill guide, and especially also for the flexible shafts, is provided for the benefit of an inexperienced user, which drill guide firmly holds the hollow grinder immovably on the removal spot by means of sharp teeth or a few needle tips.

The connection to the surgical drills is made via the coupling parts which comprise the devices for central flushing, the seal and a quick-action chuck which receives the hollow cylinders and if necessary, gearing members.

I claim:

1. A bone-grinding instrumentality powered by a rotary tool, such as a drilling machine, for use in the removal of bone material and for preparation of transplant beds, the instrumentality comprising: a first rotating hollow bone grinding cylinder for preparing bone for the removal of bone material and for preparation of transplant beds having an inner and outer wall of selected internal and external diameters, respectively and an end base having coupling means thereon being releasably joined via the coupling means to a rotary power tool and being configured at one end as a grinding head having a rounded end face; the grinding head having an end surface with an abrasive coating thereon, the abrasive coating having a particle size between 30 and 350 μm; a coolant feed line, means for attaching the coolant feed line to the instrumentality in alignment with the interior of the first hollow bone-grinding cylinder wherein the cylinder is supplied with coolant by means of the coolant feed line whereby the first bone-grinding cylinder produces a first plug of bone material for removal from the bone to leave a space therein and, a second rotating hollow bone-grinding cylinder interchangeable with the first cylinder for preparing a transplant plug from other bone for implanting in the space left by removal of the first plug.

2. A bone-grinding instrument according to claim 8, wherein the inner wall of the hollow bone-grinding cylinder has a slightly conical shape with a cross-section which decreases in the direction of the end face of the hollow cylinder.

3. A bone-grinding instrument according to claim 8, wherein the hollow bone-grinding cylinder has at least one aperture which terminates before the end face.

4. A bone-grinding instrument according to claim 8, wherein a drilling machine is provided for driving the driving member and an illumination device is included in the instrument, the illumination device facing the grinding head and having means for creating a cone of light which is focussed on the tip of the hollow cylinder.

5. The bone-grinding instrumentality of claim 1 further including a hollow, bone plug removal cylinder suitable for the removal of bone material plugs prepared by the bone-grinding cylinders the hollow, bone plug removal cylinder comprising: a rotatable hollow cylindrical portion with an inner wall and having the same internal and external diameters as the hollow bone-grinding cylinders of the bone-grinding instrumentality and including at least one catch on the inner wall thereof; whereby when the bone plug removal cylinder is pushed over the cylindrical bone material and said catch penetrates into the bone material, the hollow removal cylinder surrounding the cylindrical bone material and extracting the cylindrical bone material when the hollow removal cylinder is rotated and subsequently withdrawn.

6. The bone-grinding instrument according to claim 2 wherein the slightly conical shape provides an inside clearance angle in the range of about 5 seconds to 180 seconds.

7. The bone-grinding instrument according to claim 6 wherein the slightly conical shape provides an inside clearance angle in the range of about 20 seconds to 72 seconds.

8. A bone-grinding instrument for removal of a plug of bone material, the instrument comprising: a rotating hollow bone-grinding cylinder having an inner and an outer wall and an end base being releasibly joined via a coupling to a driving member and be configured at one end as a grinding head having a rounded end face; the grinding head having a surface with an abrasive coating thereof, the abrasive coating having a particle size between 30 and 350 μm, and the interior of the hollow bone-grinding cylinder being supplied with coolant by means of a coolant feed line.

9. A bone-grinding instrumentality according to claim 1, wherein said second rotating hollow bone-grinding cylinder also has a coupling for releasably joining to said driving member and is releasably interchangeable with the first rotating hollow cylinder, the second rotating hollow cylinder being configured like the first rotating hollow cylinder, the first rotating hollow cylinder having an external diameter in the range of 0.1 mm to 0.4 mm smaller than the internal diameter of the second rotating hollow cylinder so as to form the transplant bed to receive the transplant plug prepared by the second rotating hollow bone-grinding cylinder.

10. The bone-grinding instrumentality of claim 18, further including a hollow bone plug removal cylinder suitable for the removal of bone material plugs prepared by the bone-grinding cylinders; the hollow, bone plug removal cylinder comprising:

a rotatable hollow cylindrical portion having the same internal and external diameters as the hollow bone-grinding cylinders of the bone-grinding instrumentality and including at least one catch on the inner wall thereof; whereby when the hollow removal cylinder is pushed over the cylindrical bone material and said catch penetrates into the bone material, the hollow removal cylinder surrounding the cylindrical bone material and extracting the cylindrical bone material when the hollow removal cylinder is rotated and subsequently withdrawn.

* * * * *

UNITED STATES PATENT AND TRADEMARK OFFICE
CERTIFICATE OF CORRECTION

PATENT NO. : 4,895,146

DATED : January 23, 1990

INVENTOR(S) : Klaus Draenert

It is certified that error appears in the above-identified patent and that said Letters Patent is hereby corrected as shown below:

Column 6, line 53, delete "be", insert --being--.

Column 7, line 4, delete "claim 18", insert --claim 9--.

Signed and Sealed this

Fifteenth Day of June, 1993

Attest:

MICHAEL K. KIRK

Attesting Officer

Acting Commissioner of Patents and Trademarks